United States Patent [19]

Tsukada et al.

[11] Patent Number: 5,624,410
[45] Date of Patent: Apr. 29, 1997

[54] MAGNETIC CAP FOR MEDICAL APPLIANCE TO BE RETAINED IN HUMAN BODY

[75] Inventors: Osamu Tsukada, Nagano-ken; Satoshi Takasaka, Tokyo, both of Japan

[73] Assignee: Tsukada Medical Research Co., Ltd., Tokyo, Japan

[21] Appl. No.: 409,032

[22] Filed: Mar. 23, 1995

[30] Foreign Application Priority Data

Jul. 4, 1994 [JP] Japan ................... 6-152072

[51] Int. Cl.⁶ .................................... A61M 5/00
[52] U.S. Cl. ................ 604/256; 220/330; 604/321
[58] Field of Search ........................ 604/246, 256, 604/321, 323; 220/230

[56] References Cited

U.S. PATENT DOCUMENTS

| | | | |
|---|---|---|---|
| 2,932,545 | 4/1960 | Foley | 220/230 |
| 3,468,576 | 9/1969 | Beyer et al. | 220/230 |
| 4,060,100 | 11/1977 | Miller et al. | 220/230 |
| 4,110,552 | 8/1978 | Lombardi | 220/230 |
| 4,338,937 | 7/1982 | Lerman . | |
| 4,417,890 | 11/1983 | Dennehey et al. | 604/256 |
| 4,443,219 | 4/1984 | Meisch et al. | 604/256 |
| 4,706,834 | 11/1987 | Farney et al. | 220/230 |
| 4,963,132 | 10/1990 | Gibson | 604/256 |
| 5,098,405 | 3/1992 | Peterson et al. | 604/256 |
| 5,263,944 | 11/1993 | Vidal et al. | 604/256 |

FOREIGN PATENT DOCUMENTS

| | | | |
|---|---|---|---|
| 2255044 | 12/1974 | France . | |
| 2551010 | 5/1977 | Germany . | |
| 3921540 | 6/1989 | Germany | 220/230 X |
| 1167055 | 6/1989 | Japan | 220/230 X |
| 658438 | 11/1986 | Switzerland . | |

*Primary Examiner*—Robert A. Hafer
*Assistant Examiner*—N. Kent Gring
*Attorney, Agent, or Firm*—Sughrue, Mion, Zinn, Macpeak & Seas

[57] ABSTRACT

This invention makes it easy to operate for a medical appliance to be retained in a human body. The magnetic cap (10) includes an annular magnet (2) secured to an upper face of a connecting plug body (1); a disk like magnet (4) secured to an upper face of a lid body which is detachably coupled to the connecting body (1) through a flexible band (6); and a strap (5) attached to an end of the lid body (3). The magnets (2) and (4) are set to be 5 to 15 mm in diameter, 0.5 to 5.0 mm in thickness, and 1500 to 2000 gauss in magnetic flux density. Magnetic poles on contact faces of the magnets (2) and (4) are directed in opposition to each other.

4 Claims, 2 Drawing Sheets

MAGNETIC CAP FOR MEDICAL APPLIANCE TO BE RETAINED IN HUMAN BODY

BACKGROUND OF THE INVENTION (1) Field of the Invention

This invention relates to a magnetic cap which serves as an external switch valve for a medical appliance to be retained in a human body (for example, a urethra catheter and the like).

(2) Statement of the Prior Art

Heretofore, there are the following examples of medical appliances which are retained in a human body.

Various diseases involving incontinence affect women. Medical therapy including ubrechide, α-blocker and the like may be applied and an intermittent self-withdrawing method are now also widely effected. Also, a medical therapy (anticholine agent, imipramine, ephedrine hydrochloride, α actuation agent or the like), a balloon catheter retaining method, pelvis lower muscle training method, intermittent self-withdrawing method, urination method using a urine collector or various kinds of napkins, and the like are also employed in cases of incontinence. These methods have provided substantial benefits.

On the other hand, in the case of damage to cerebral blood vessels on the spinal cord, medication may be slow and people thus afflicted may have difficulty using a catheter, consequently the above method, are not often applied to these persons. In particular, women suffering paralysis having diseases worse than a middle degree and upper spinal cord (higher than seventh cervical vertebrae) damaged women are treated only by a selectable urination control method such as utilization of urinary bladder bags or napkins.

SUMMARY OF THE INVENTION

An object of the present invention is provide a magnetic cap for a medical appliance to be retained in a human body, which can be readily handled for charging and discharge urine even by, for example, women who retain urine in their bladders find it difficult to discharge the urine also for women who are unable to use urinary bladder bags or napkins.

A magnetic cap for a medical appliance to be retained in a human body in accordance with the present invention, comprises: an annular magnet secured to an upper face of a connecting plug body; a disk like magnet secured to an upper face of a lid body which is detachably coupled to the connecting body through a flexible band; and a strap attached to an end of the lid body. The annular and disk like magnets are set to be 5 to 15 mm in diameter, 0.5 to 5.0 mm in thickness, and 1500 to 2000 gauss in magnetic flux density. Magnetic poles on contact faces of the annular and disk like magnets are directed in opposition to each other.

In the magnetic cap for a medical appliance to be retained in a human body in accordance with the present invention, when a disabled patient hooks the strap to their palm or finger to bring the two magnets together, the magnets become attached under their magnetic forces.

Since both magnets are set to be 1500 to 2000 gauss in magnetic flux density, a mutual attraction force of the magnets becomes stronger and the cap is not disconnected from the connecting plug body in use. However, in the case that the patient wants to disconnect the cap, the patient can easily detach the cap from the plug body only be pulling the strap using their palm or finger.

Since it is possible to detachably connect the connecting plug body to a port of the medical appliance to be retained in the human body, the magnetic cap can be applied to the same or different kind of appliance.

Since both magnets are set to be 5 to 15 mm in diameter and 0.5 to 5.0 mm in thickness, the magnetic cap becomes relatively small size and does not impart any discomfort to the patient.

DETAILED DESCRIPTION OF THE PREFERRED EMBODIMENTS

Figure 1:
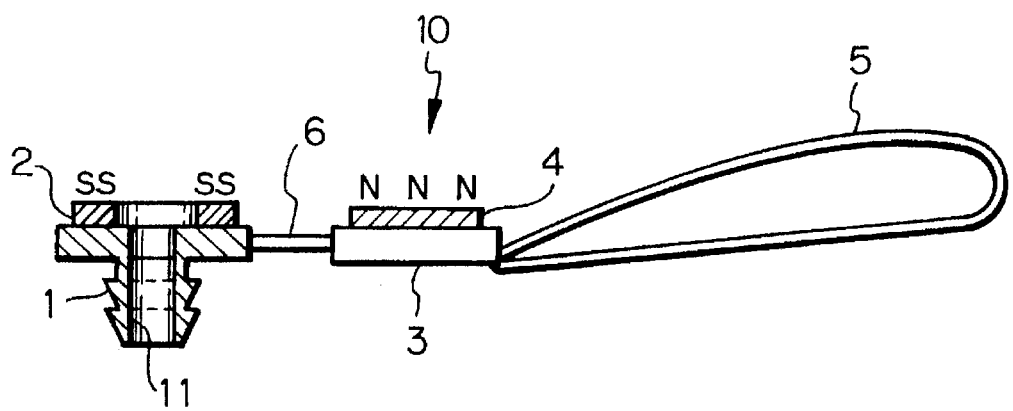
FIG. 1 is a longitudinal sectional view of a magnetic cap of the present invention.

Referring now to FIGS. 1 through 3A and 3B, a magnetic cap 10 for a medical appliance to be retained in a human body in accordance with the present invention will be explained below.

The magnetic cap 10 for a medical appliance to be retained in a human body, comprises: an annular magnet 2 secured to an upper face of a connecting plug body 1; a disk like magnet 4 secured to an upper face of a lid body which is detachably coupled to the connecting body 1 through a flexible band 6; and a strap 5 attached to an end of the lid body 3.

The magnets 2 and 4 are set to be 5 to 15 mm in diameter, 0.5 to 5.0 mm in thickness, and 1500 to 2000 gauss in magnetic flux density. Magnetic poles on contact faces of the magnets 2 and 4 are directed in opposition to each other. In the illustrated embodiment, the upper and lower faces of the annular magnet 2 are set to be an S-pole and an N-pole while the upper and lower faces of the disk like magnet 4 are set to be an N-pole and an S-pole.

Figure 2:
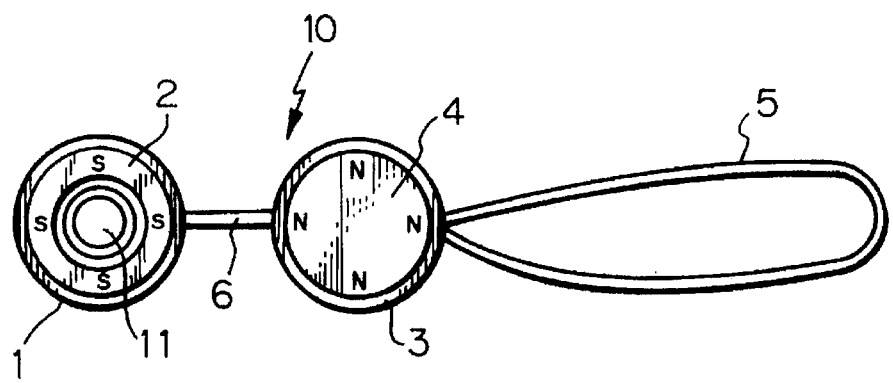
FIG. 2 is a plan view of FIG. 1.

As shown in FIGS. 1 and 2, when the magnetic cap 10 is in an open position the annular magnet 2 releases a passage 11 in the connecting plug body 1 while the disk like magnet 4 is spaced away from the body 1.

Figure 3A:
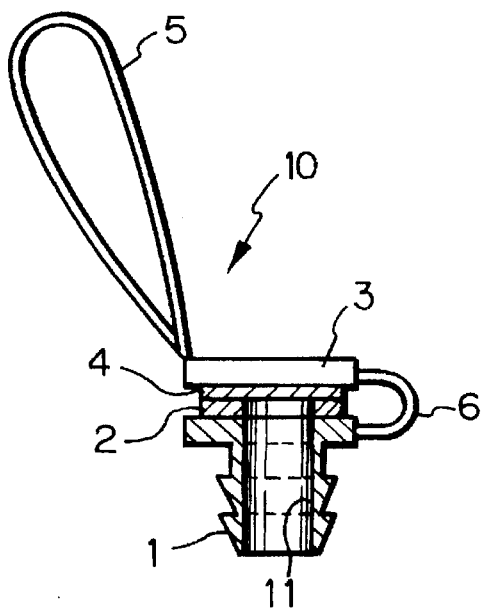
FIG. 3A is a longitudinal sectional view of the magnetic cap, illustrating a closed state of the cap shown in FIG. 1.
Figure 3B:
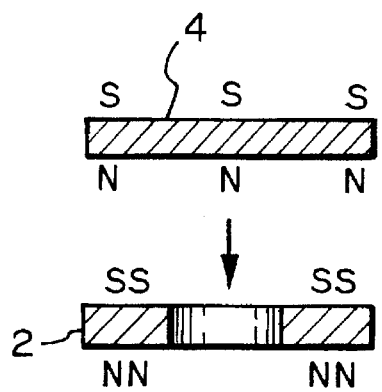
FIG. 3B is a longitudinal sectional view of a pair of magnets, illustrating an open position of the magnets.

As shown in FIG. 3A, when the magnetic cap is in a closed position, both magnets 2 and 4 contact with each other and attracts each other by their magnetic forces. As shown in FIG. 3B, both magnets are aligned with the same center axis by their attraction forces immediately before the magnets contact with each other.

In the case that one of the magnets 2 and 4 is made of an iron material, they immediately contact with each other when they approach each other and thus they cannot adjust misalignment of their center axes automatically.

When the magnetic cap 10 is in the closed position as shown in FIG. 3A, the disk like magnet 4 closes the passage 11 in the connecting plug body 1.

Figure 4A:
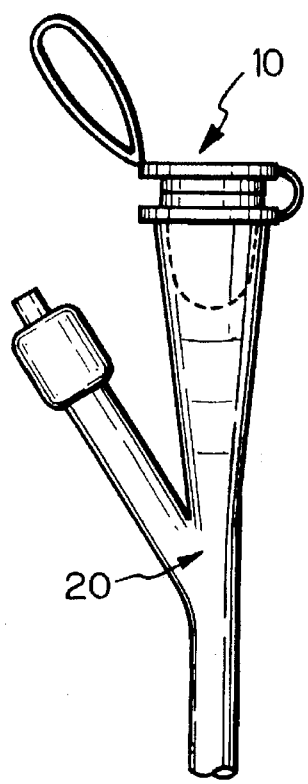
FIGS. 4A and 4B are side elevational views of medical appliances to be retained in a human body, illustrating examples of using the magnetic caps.
Figure 4B:
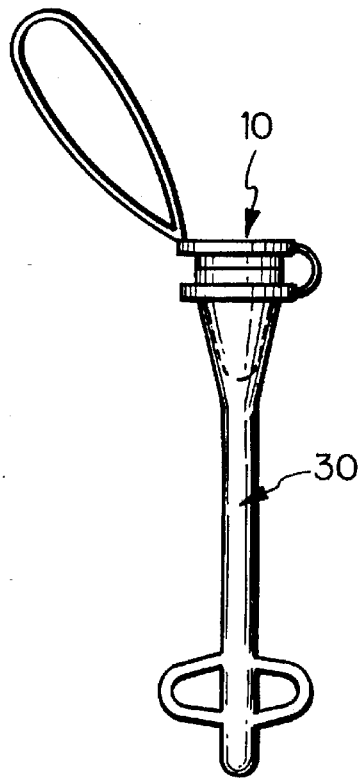

The magnetic cap 10 may be used as shown in FIGS. 4A and 4B. FIG. 4A shows an example in which the magnetic cap 10 is attached to an external drain port of an usual urethra catheter 20. FIG. 4B shows another example in which the magnetic cap 10 is attached to an external drain port of an usual MALECOT catheter 30.

Figure 5:
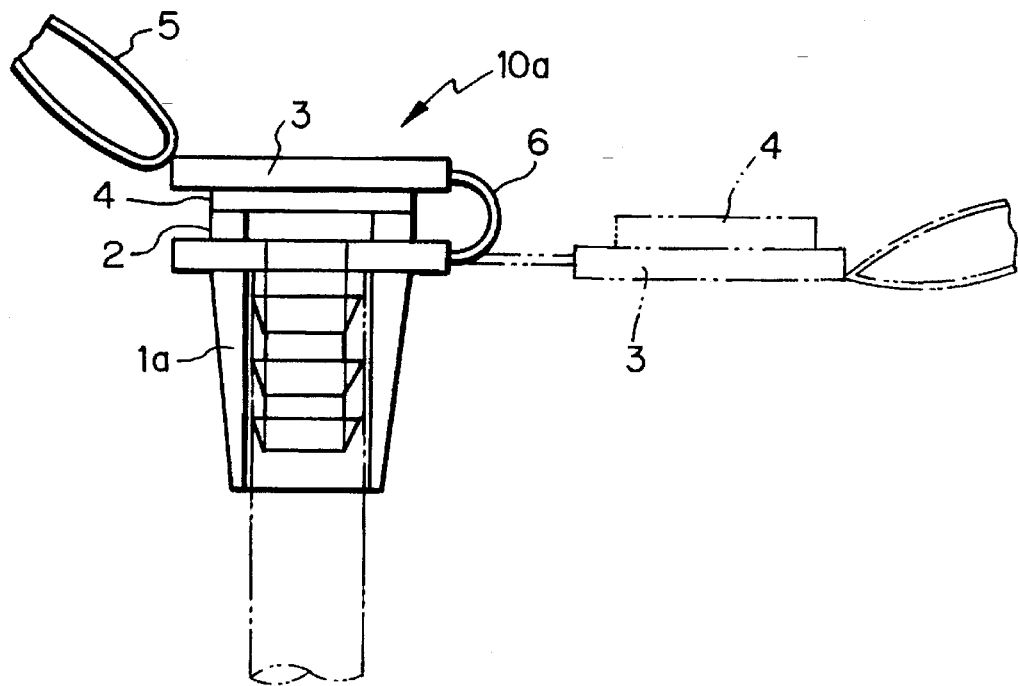
FIG. 5 is a longitudinal sectional view of an alternation of the magnetic cap of the present invention.

Although the connecting plug body shown in FIGS. 1 to 4 is coupled to an inside of a port of a mating appliance, a connecting plug body 1a with a magnetic cap 10a shown in FIG. 5 is coupled to the outside of the port.

A medical appliance, in particular, a MALECOT catheter to which the magnetic cap of the present invention can be applied is limited to the following diseases of patients:

1. It is preferable that the patient has a desire to urinate. It is not suitable for use in cases of dementia.
2. The patient can bring one's finger to the vulva.
3. A capacity of the urinary bladder must be more than 150 ml.
4. The patient can take a balance upon opening the legs and setting on the legs.
5. It is not suitable for the patient who has an external port of the urethra in one's inner part or has pronounced vagina atrophy.
6. It is not suitable for a patient who feels that a balloon catheter retained in the body is an obstacle.
7. The patient may take a bath.
8. It is applicable for a patient who has difficulty in moving ones fingers, has urination diseases or urine storage diseases.
9. The patient can urinate at a toilet under a condition similar to natural urination.

The magnetic cap of this invention can be utilized to a medical appliance to be retained in a human body over a wide scope, is simple in operation, and is superior in a closing function. Further, the cap has a simple construction and can be made at a low production cost.

What is claimed is:

1. A magnetic cap for medical appliance to be retained in a human body, comprising:
   a connecting plug body having an upper face;
   an annular magnet secured to said upper face of said connecting plug body which is adapted to be removably secured to the medical appliance;
   a lid body having an upper face;
   a disk like magnet secured to said upper face of said lid body which is detachably coupled to said connecting plug body through a flexible band secured to said lid body at a first radial position, each of said magnets having a contact face; and
   a strap attached to an end of said lid body at a second radial position substantially opposing said first radial position such that said lid body can be detached from said connecting plug body;
   wherein said magnets contact each other along respective contact faces, magnetic poles on said contact faces of said annular and disk like magnets being directed in opposition to each other.

2. The magnetic cap of claim 1, wherein said connecting plug body is insertable into a drain hole provided in said medical appliance.

3. The magnetic cap of claim 1, wherein said connecting plug body includes attaching means for circumscribing a spout of said medical appliance in which a drain hole is formed.

4. The magnetic cap of claim 1, wherein said annular and disk like magnets is set to be 5 to 15 mm in diameter, 0.5 to 5.0 mm in thickness, and 150 to 2000 gauss in magnetic flux density.

* * * * *